(12) United States Patent
Forney et al.

(10) Patent No.: US 7,001,571 B2
(45) Date of Patent: Feb. 21, 2006

(54) SYSTEMS AND METHODS FOR DISINFECTION

(75) Inventors: Larry Forney, Doraville, GA (US);
John Pierson, Marietta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 10/692,983

(22) Filed: Oct. 24, 2003

(65) Prior Publication Data

US 2004/0126273 A1 Jul. 1, 2004

Related U.S. Application Data

(60) Provisional application No. 60/461,326, filed on Apr. 8, 2003, provisional application No. 60/420,985, filed on Oct. 24, 2002.

(51) Int. Cl.
*A61L 2/00* (2006.01)
(52) U.S. Cl. .................... 422/22; 210/780; 250/435; 250/455.11; 422/24; 422/186.3; 422/900
(58) Field of Classification Search .............. 422/22, 422/24, 186.3, 186, 900; 210/780; 250/455.11, 250/435
See application file for complete search history.

(56) References Cited

U.S. PATENT DOCUMENTS

| | | | |
|---|---|---|---|
| 4,963,750 A * | 10/1990 | Wilson | 250/436 |
| 5,279,463 A | 1/1994 | Holl | 241/1 |
| 5,335,992 A | 8/1994 | Holl | 366/348 |
| 5,439,652 A | 8/1995 | Sczechowski et al. | 422/186.3 |
| 5,538,191 A | 7/1996 | Holl | 241/1 |
| 5,993,674 A * | 11/1999 | Rolchigo et al. | 210/780 |
| 6,015,229 A | 1/2000 | Cormack et al. | 366/336 |
| 6,471,392 B1 | 10/2002 | Holl et al. | 366/279 |
| 6,576,201 B1 * | 6/2003 | Woo et al. | 422/186 |

OTHER PUBLICATIONS

L.J. Forney and J.A. Pierson *Photolytic Reactors: Similitude in Taylor—Couette and Channel Flows*. AiChE Journal, vol. 49, No. 5, pp. 1285-1292 (May 2003).

Cho, I.H., Moon, I.Y., Chung, M.H. et al. Disinfection Effects of *E. coli* Using $TiO_2$/UV and Solar Light System. Water Science and Technology: Water Supply, vol. 2, No. 1, pp. 181-190 (2002).

Lyn, D.A., Chiu, K. and Blatchley, E.R. Numerical Modeling of Flow and Disinfection in UV Disinfection Channels. Journal of Environmental Engineering, pp. 17-26 (1999).

Matsunaga, T. and Okochi, M. TiO2-Mediated Photochemical Disinfection of *Escherichia coli* Using Optical Fibers. Environmental Science & Technology, vol. 29, No. 2 (1995).

Miller, R.L., Fredrickson, A.G., Brown, A.H. et al. Hydromechanical Method to Increase Efficiency of Algal Photosynthesis. I&EC Process Design and Development, vol. 3, No. 2, pp. 134-143 (1964).

Scheible, K.O. Development of a Rationally Based Design Protocol for the Ultraviolet Light Disinfection Process. Journal WPCF, vol. 59, No. 1, pp. 25-31 (1987).

(Continued)

*Primary Examiner*—Krisanne Jastrzab
(74) *Attorney, Agent, or Firm*—Thomas, Kayden, Horstemeyer & Risley LLP; Todd Deveau

(57) ABSTRACT

Methods and systems for establishing Taylor-Couette flow in a fluid are provide. Aspects of the disclosed methods and systems incorporate Taylor-Couette flow in combination with a source of radiation to provide more uniform radiation exposure to the fluid and its components. Common problems of non-uniform radiation levels and concentration boundary layer effects in UV reactors are largely eliminated using the methods and devices provided herein.

17 Claims, 14 Drawing Sheets

OTHER PUBLICATIONS

Sczechowski, J.G. A Taylor Vortex Reactor for Heterogeneous Photocatalysis. Chemical Engineering Science, vol., 50, No., 20, pp. 3163-3173 (1995).

Severin, B.F., Suidan, M.T. and Engelbrecht, R.S. Kinetic Modeling of U.V. Disinfection of Water. Water Res., vol. 17, No. 11, pp. 1669-1678 (1983).

* cited by examiner

SYSTEMS AND METHODS FOR DISINFECTION

CROSS REFERENCE TO RELATED APPLICATIONS

This application claims benefit of U.S. Provisional Patent Application No. 60/420,985 filed on Oct. 24, 2002, and to U.S. Provisional Patent Application No. 60/461,326 filed on Apr. 8, 2003, both of which are incorporated by reference in their entirety.

BACKGROUND

1. Technical Field

The present disclosure is related generally to methods and systems for moving fluids, more particularly, methods and systems for generating fluid flow that increases fluid exposure to an energy source for sterilization or disinfection.

2. Related Art

Water use is a major environmental concern and methods to reduce and reuse water consumption are in demand. In food processing facilities, water shortages have made water reclamation and reuse an integral component of environmental programs. To ensure that re-used effluents do not pose an unreasonable risk to public health, the Environmental Protection Agency (EPA) has outlined strict regulations for water reclamation. These water disinfection regulations provide a substantial public health benefit by reducing discharges of many waterborne pathogenic organisms to water supplies, recreational water, shellfish water and other waters that can potentially transmit disease to humans.

Many technologies exist for bacterial destruction in water reclamation such as chlorination which is a relatively low cost disinfection process. Chlorine treatment, however, presents a number of problems. For example, chlorine disinfection is incapable of achieving appreciable inactivation of the several viruses and protozoa, specifically, *Cryptosporidium parvum* at reasonable disinfectant doses and contact times (Sobsey, M. D. (1989). *Inactivation of health-related microorganisms in water by disinfection processes*. Wat Sci. Tech. 21:179–195). In addition, large chlorine concentrations generate chloro-organic, disinfection by-products such as trihalomethanes (THMs) and other carcinogens that persist in the environment (Matsunaga, T., and M. Qkochi. (1995). *TiO₂-Mediated Photochemical Disinfection of Escherichia coli Using Optical Fiber*. Environ. Sci. Technol. 29:501–505).

Due to the environmental concerns associated with chemical disinfection, current water treatment methods are moving away from traditional chemical to physical procedures (Cho, I. H. et al. (2002). *Disinfection effects E. coli using TiO₂ AJV and solar light system*. Wat. Sci. and Tech. 2: 181–190). For example, use of ultraviolet (UV) radiation is becoming more popular for wastewater treatment since it is effective against both bacteria and viruses, leaves no residues and is economical (Wong, E. et al. (1998). Reduction of *Escherichia coli* and *Salmonella senftenberg* on pork skin and pork muscle using ultraviolet light. Food Microbiology. 15:415–423). UV processing uses radiation in the germicidal range from 200 to 280 nm to generate DNA mutations within pathogens (Federal Department of Agriculture and Center for Food Safety and Applied Nutrition. (2000). *Kinetics of microbial inactivation for alternative food processing technologies: Ultra-violet light*). The latter study also concludes that to achieve microbial inactivation, the UV radiant exposure must be at least 400 J/m² in all parts of the product. Moreover, UV irradiation is particularly effective when it is used in conjunction with powerful oxidizing agents such as ozone and hydrogen peroxide.

Treatment of fluid flow is also important in food processing for example in processing of beverages such as milk, juices, alcoholic drinks or soft drinks. Existing methods for treating fluid foodstuffs typically include exposing the foodstuffs to high temperatures in an effort to neutralize potentially harmful bacteria. Unfortunately, thermal treatment of foodstuff can cause the breakdown of ingredients including proteins and vitamins. The United States Food and Drug Administration (US-FDA) has recently published a ruling (21 CFR 179) that approves the use of UV radiation in place of pasteurization.

Early modeling of disinfection efficiencies in flow-through UV reactors focused on the ideal designs of either a completely mixed (stirred tank) or plug flow configurations (Haas, C. N. and Sakellaropoulos, G. P. (1979). *Rational analysis of ultraviolet disinfection reactors*, Proceedings of the National Conference on Environmental Engineering, American Society of Civil Engineering, Washington, D.C.; Severin, B. F. et al. (1984) *Kinetic modeling of UV disinfection of water. Inactivation kinetics in a flow-through UV reactor*, J WPCF. 56:164–169). As summarized by the Water Environment Federation (Water Environment Federation (1996). *Wastewater Disinfection Manual of Practice FD-10*, chapter 7, Alexander, Va.), Scheible (Scheible, O. K. (1987). *Development of a rationally based design protocol for the ultraviolet disinfection process*. J. Water Pollution Control Fed. 59:25–31) developed a model to account for non-ideal reactor theory that requires four empirical constants. A strictly empirical model was also proposed by Emerick and Darby (Emerick, R. W. and Darby J. L. (1993). *Ultraviolet light disinfection of secondary effluents: predicting performance based on water quality parameters*. Proc. Plann. Des. and Oper. Effluent Disinfection Syst. Spec. Conf., Water Environment Federation, Whippany, N.J., p. 1 87) to account for a number of factors that influence water quality. Recently, computational fluid dynamic (CFD) solutions have provided insight into the turbulent flow characteristics of UV reactors (Lyn, D. A. et al. in E.R. (1999). *Numerical Modeling of flow and disinfection in UV disinfection channels*, J Environ. Eng. 125, 17–26).

Of the two ideal designs and considering a single reaction, it is well established that plug flow provides comparable yield but with a substantial reduction in holdup volume that can exceed two orders of magnitude compared to a completely mixed reactor (Levenspiel, O. (1972). Chemical Reaction Engineering, 2$^{nd}$ Ed., John Wiley and Sons, Inc., New York, N.Y.). For such plug flow designs, the surface-to-volume ratio is large which is favorable to the transmission of UV radiation through the reactor walls and contained fluid. The major limitations to plug flow designs, however, are both non-uniform radiation intensities within the fluid and low concentrations of absorbing species such as viable pathogens near irradiated walls. The effects of the latter are reduced by increasing the flow rate thus reducing the velocity and concentration boundary layer thickness but, unfortunately, also the residence time and thus the radiation dosage.

Previous studies on the effects of radiation in Taylor-Couette flow are the growth of algae (Miller, R. L. et al. (1964). *Hydromechanical method to increase efficiency of a lgal photosynthesis*, Ind. Engng. Chem. Process Des. Dev. 3:134) and the development of a reactor for heterogeneous photocatalysis (Sczechowski, J. G. et al. (1995). *A Taylor vortex reactor for heterogeneous photocatalysis*, Chem. Eng. Sci. 50:3163).

Recently, the inventors herein (Forney, L. J., and Pierson J. A., (2003), *Optimum photolysis in Taylor-Couette flow*, AIChE 1.49:727–733; Forney, L. J. and Pierson, J. A. (2003), *Photolylic reactors: similitude in Taylor-Couette and channel flows*, AIChE J. 49:1285–1292, both of which are incorporated by reference in their entirety as if fully set forth herein) considered a fast photolytic reaction and demonstrated that optimum photoefficiencies could be achieved if the radiation penetration depth were controlled in relation to the velocity, boundary layer thickness. Their latter work also provided a scaling law for the yield in both Taylor-Couette and channel flows.

Thus, there is a need for systems and methods for the non-thermal processing of fluids.

There is another need for systems and methods for the non-thermal control of micro-organisms in edible fluids.

SUMMARY OF THE INVENTION

Methods and systems for establishing Taylor-Couette flow in a fluid are provided. Aspects of the methods and systems are useful for the irradiation of microorganisms in the fluid. Exemplary methods and systems incorporate Taylor-Couette flow in combination with a source of radiation. Such a combination can provide more uniform radiation exposure to the fluid and components of the fluid.

One aspect provides a method and system for disinfecting a fluid that includes introducing a fluid containing an organism, for example a micro-organism, into a reactor. The reactor typically includes a rotor having an outer wall. The rotor is housed within an outer cylinder. The outer cylinder includes an inner annular wall. The outer wall of the rotor and the inner wall of the outer cylinder define a first annular channel or gap. The outer cylinder also includes an inlet and an outlet in fluid communication with the annular channel or gap. An electromagnetic energy source is associated with the outer cylinder for irradiating the fluid in the annular channel or gap with an anti-microbial amount of electromagnetic energy. When the reactor is filled with fluid to be sterilized or disinfected, the rotor speed is controlled to create laminar Taylor Couette flow (laminar vortices) in the fluid in the annular channel or gap. The rotor speed can be regulated with a controller that can vary the rotation of the rotor to form laminar vortices in the fluid, for example inducing Taylor numbers in the fluid of about 40 to about 400. Controllers are known in the art and conventional controllers can be used so long as they can control the rotor to induce laminar vortices or Taylor numbers of about 40 to about 400. A further embodiment includes a second annular channel or gap interior of the outer wall of the rotor providing a second annular channel or gap for receiving the fluid. The first and second annular channels being in communication with each other.

An exemplary method for irradiating a fluid includes inducing Taylor vortices in a fluid containing an organism, for example by generating a Taylor number in the fluid of between about 40 to about 400 (representing laminar Taylor vortices); and irradiating the fluid with an anti-microbial amount of energy. The anti-microbial amount of energy can be ultraviolet light in an amount sufficient to kill or inhibit microbial growth in the fluid or render the fluid safe for human consumption. Suitable fluids include, but are not limited to, foodstuffs such as beverages, milk, juice, soft drinks, or alcoholic beverages, and waste water. In another embodiment, the ratio of the penetration depth of the energy to the velocity boundary layer thickness in the fluid is less than about 1, more preferably from about 0.5 to about 1.

Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION

Embodiments of the present disclosure provide methods and systems for producing Taylor-Couette flow in a fluid. The fluid can be exposed to an energy source, for example an electromagnetic energy source such as an ultraviolet light emitting lamp or other non-thermal energy source. Suitable UV lamps emit radiation in the range of about 200–400 nm, preferably about 200–280 nm. The exposure of the fluid to the energy source can also catalyze a chemical reaction in the fluid or in components of the fluid. One embodiment provides a system and method of irradiating a fluid in the absence of a catalyst. Additionally, irradiating the fluid with energy can kill or inhibit the growth of organisms such as microorganisms, in the fluid. The term "organism" includes single and multicellular animals, viruses, protozoa, bacteria, fungi, pathogens, and the like.

Figure 2:
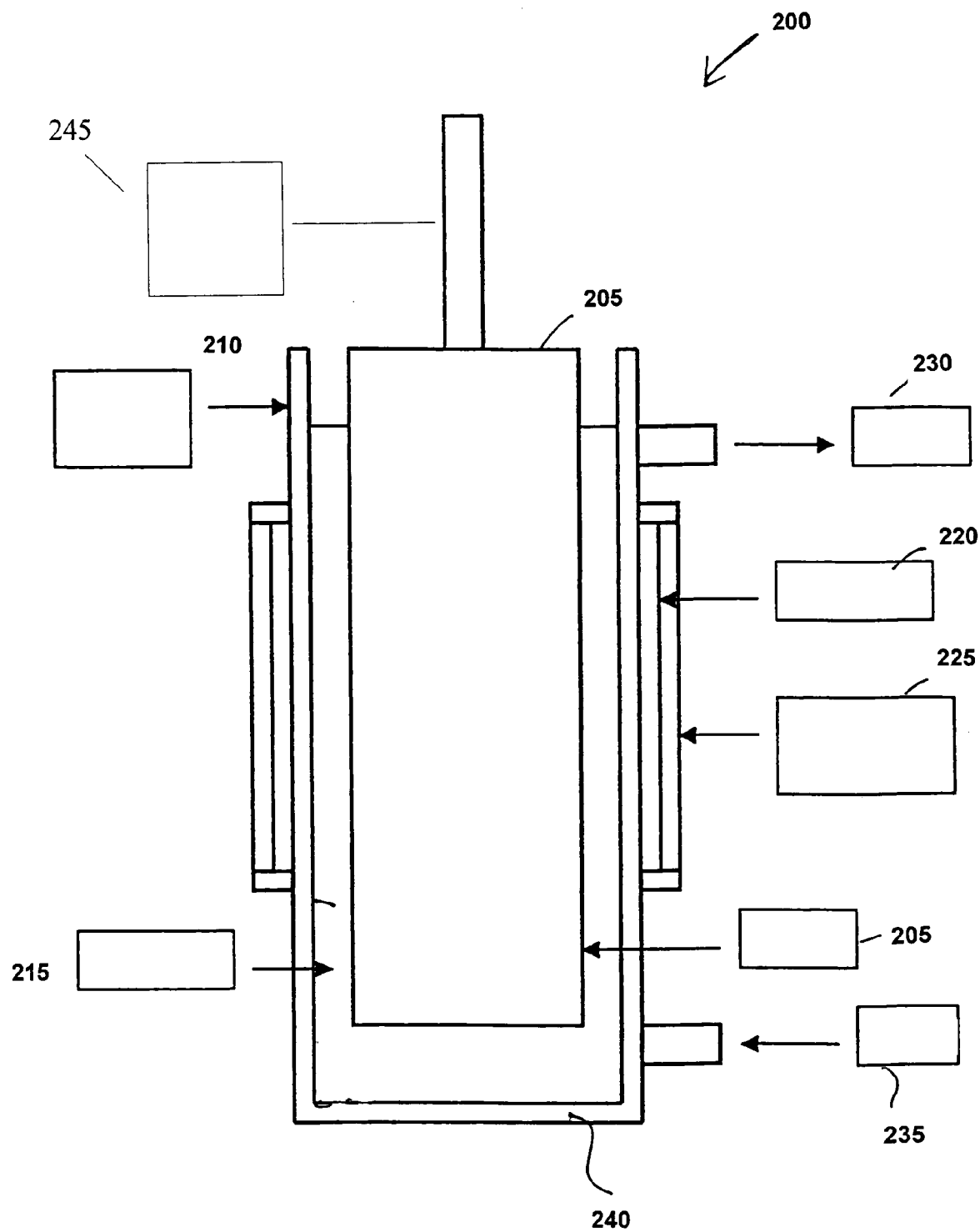
FIG. 2 is cross-sectional view of an exemplary embodiment of a system for disinfecting or sterilizing a fluid including Taylor—Couette reactor.

In one embodiment, the flow characteristics of the fluid approach that of plug flow but with a residence time that is uncoupled from the hydrodynamics or boundary layer characteristics. For example, one exemplary system of the present invention includes an inner cylinder that rotates within a stationary but larger outer cylinder as shown in FIG. 2 (Schlichting, H. (1979) Boundary Layer Theory, $7^{th}$ Ed. McGraw-Hill Book Co, NY). At low rotation rates a laminar, hydrodynamic configuration called Taylor-Couette flow is established consisting of a system of circumferential vortices within the annular fluid gap. The latter constitutes a spatially periodic flow that is the hydrodynamic equivalent to cross flow over a tube bank or lamp array. These vortices provide radial mixing, reduce the boundary layer thickness and are independent of the axial flow rate and thus the fluid residence time. An additional feature of the rotating design is the repetitive exposure of the fluid parcels to a minimum number of energy sources, for example lamps, which substantially reduces the maintenance requirements. This repetitive exposure also provides a cummulative exposure to radiation more efficiently and effectively than the application of a single dose. A further embodiment provides systems and methods for irradiating a fluid by inducing laminar vortices in the fluid, for example by inducing fluid Taylor numbers in the range of about 40 to about 400. Laminar vortices can be formed in the fluid by introducing the fluid into the disclosed reactors, for example a reactor having a rotor within a hollow cylinder.

Figure 1A:
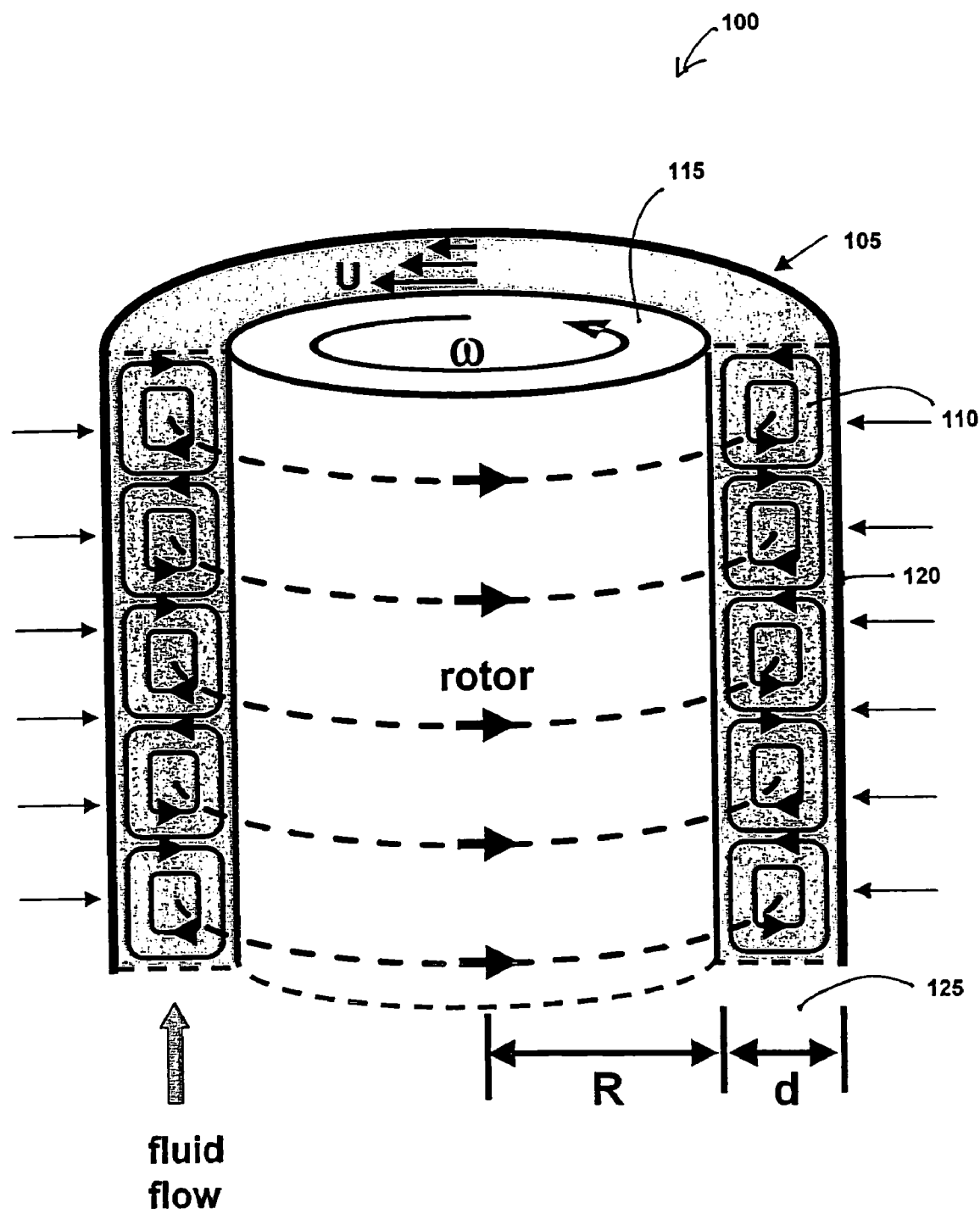
FIG. 1A is an illustration of Taylor vortices between two concentric cylinders. Inner cylinder rotating, outer cylinder at rest; d–width of annular gap; L–cylinder; R=cylinder radius.
Figure 1B:
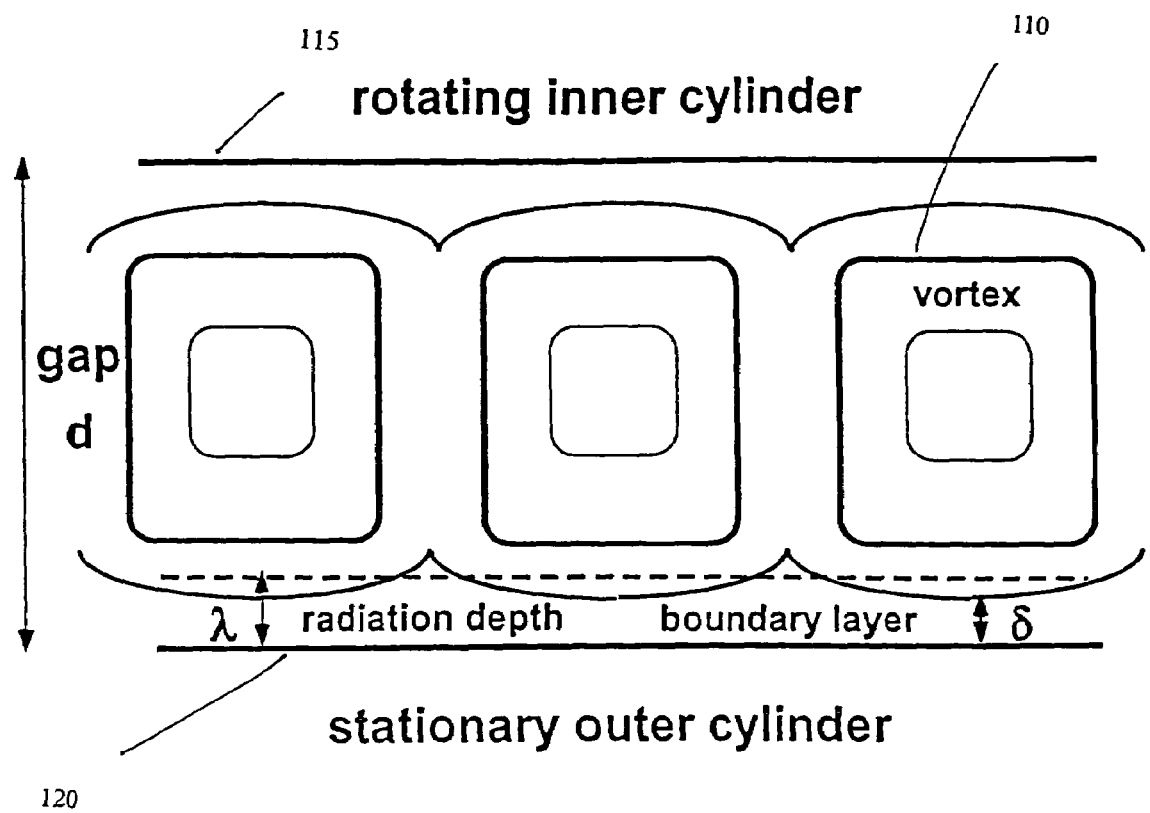
FIG. 1B is an expanded view of Taylor vortices of FIG. 1A.

An exemplary reactor is shown in FIG. 2. The reactor includes rotor 205 positioned within an inner hollow of an outer cylinder 240. An annular fluid gap 215 is formed between the inner cylinder of rotor 205. When the rotor rotates within the inner hollow of outer cylinder 240, Taylor-Couette flow is produced in the fluid within annular fluid gap 215. The circumferential vortices 110 produced in the fluid cause parcels in the fluid to rotate as shown in FIG. 1. The rotation of the parcels permits the parcels to be repeatedly exposed, for example, to an energy source 220. To maximize the exposure of energy, such as ultraviolet light, to the parcels, a reflector 225 can be placed around the exterior surface of energy source 220 to redirect scattered energy into the fluid. The reflector can be made of any reflective material including metals such as aluminum, tin, silver, glass, or a conventional mirror. The outer cylinder typically has walls 210 composed of material that enables energy such as ultraviolet light to pass therethrough without an appreciable loss of energy due to absorption, refraction, or reflection. Suitable wall material includes quartz, glass, and synthetic polymers, and may include any transparent medium.

Fluid enters the reactor via inlet 235, which is optionally positioned at the base of outer cylinder 240. When rotor 205 is actuated to begin rotating, Taylor-Couette flow is established. Fluid exits the reactor through outlet 230, optionally positioned at or near the top of outer cylinder 240. The fluid can be any fluid including water, solutions, bodily fluids such as blood and the like, wastewater, effluent, wash water, and other waste water, or fluid foodstuffs including, but not limited to milk, juice, soft drinks, nutrient drinks, diet supplements, and alcoholic drinks etc. The fluid can be irradiated by the energy source to facilitate chemical reactions in or with the fluid. Alternatively, irradiation of the fluid with energy from energy source 220 can serve to disinfect or sterilize the fluid. In one embodiment, the irradiation energy is not in the form of heat. Embodiments of the present invention advantageously preserve the activity of endogenous nutrients and enzymes in the fluid by using anti-microbial amounts of non-thermal energy.

Figure 3:
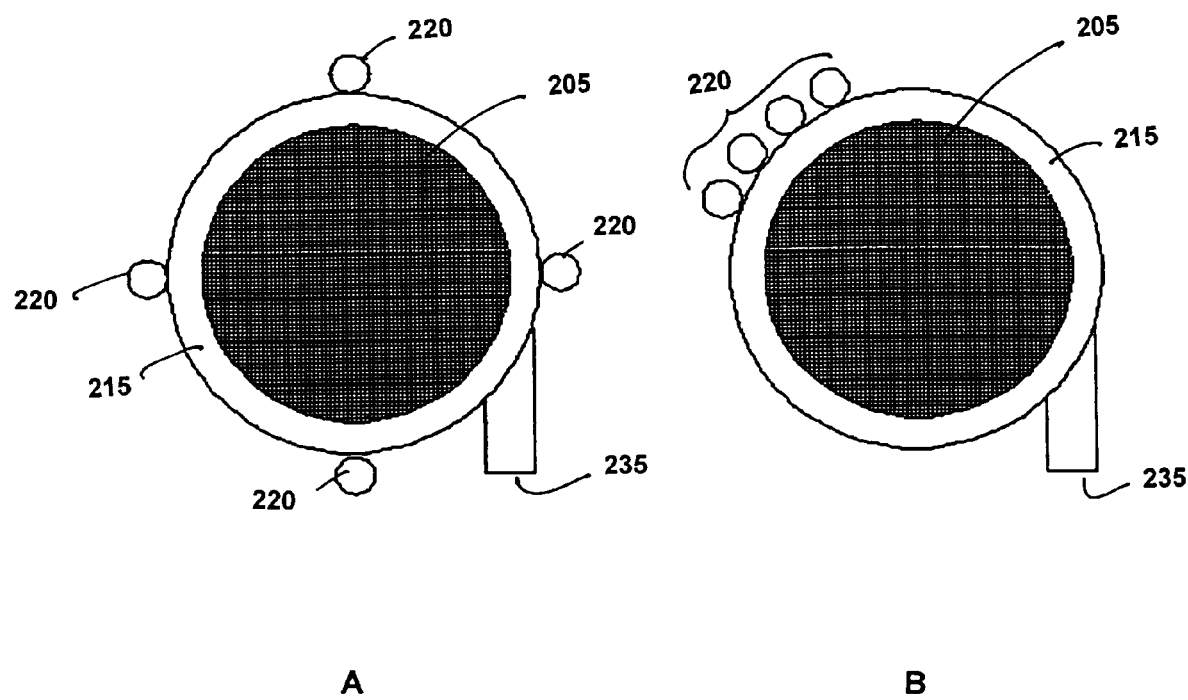
FIG. 3 is a cross section of an exemplary Taylor—Couette reactor showing symmetric and grouped irradiating lamp configurations.

In another embodiment, at least one energy source 220 is positioned tangentially to the outer cylinder wall 210. Suitable energy sources include electromagnetic energy sources including microwave energy sources, ultraviolet light sources, sound wave sources, visible light sources, infra-red light sources, X-ray sources, gamma ray sources, electron sources, atomic and sub-atomic particle sources, and the like. FIG. 3A illustrates another exemplary embodiment of the reactor having a plurality of energy sources 220 positioned equidistant around the outer cylinder 210. It will be appreciated that the energy sources can be placed in any position around the annular fluid gap 215 such that the energy emitted from the energy source 220 is directed into the fluid in the annular fluid gap 215. FIG. 3B shows a plurality of energy sources 220 positioned opposite inlet 235.

Figure 4:
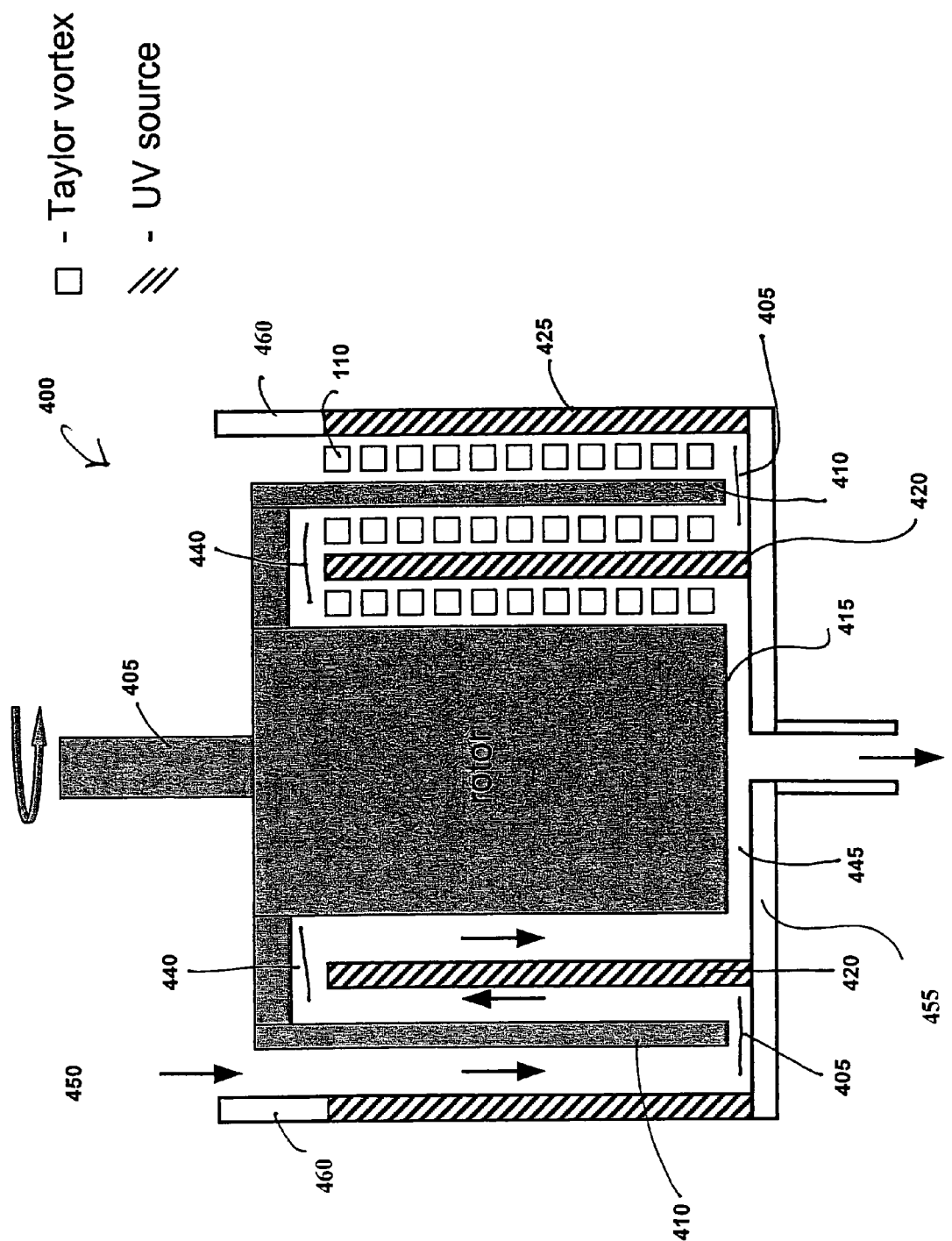
FIG. 4 is a cross section of another embodiment of the present invention.

FIG. 4 is a cross-sectional side view of still another embodiment of the present disclosure. In this embodiment, fluid enters the reactor through inlet 450 which is in fluid communication with an annular channel 405a. Inner annular channel 405a is in fluid communication with inner hollow 445. The reactor includes rotor 405 having an annular channel 440 between an outer wall 410 and an inner cylinder 415. Rotor 405 is housed or positioned within outer cylinder 240 such that the outer wall 410 of rotor 405 separates annular channel 405a.

Outer cylinder 455 includes an inner annular wall 420 defining a circular hollow 445 for receiving inner cylinder 415 of rotor 405. Outer annular wall 460 defines annular channel 405a between outer annular wall 460 and inner annular wall 420. Annular channel 405a receives outer wall 410 of rotor 405. Annular wall 420 also separates annular channel 440 when rotor 405 is positioned within outer cylinder 455. Fluid traverses through the annular channels and exits through outlet 430. Outlet 430 is optionally positioned at the base of outer cylinder 455, for example in the center of the base of outer cylinder 455 and opposite inner cylinder 415. As the fluid traverses the annular channels, it is moved through multiple circumferential vortices exposing the fluid and particles in the fluid to energy source 425. The design illustrated in FIG. 4 has three continuous fluid channels of equal length. This design allows for the same number of vortices as a design having a single annular channel three times the height as one of the channels of FIG. 4. The design of FIG. 4 allows for a shorter rotor and reactor. Alternatively, two or more annular channels can be provided.

Energy source 425 can be integral with annular walls 460, 410, 420, or a combination thereof. Alternatively, energy source 425 can be removably affixed to annular walls 460, 410, 420, or a combination thereof or can form all or part of the walls. Energy from energy source 425, such as ultraviolet light, can irradiate fluid as the fluid traverses annular channels 405a and 440. Taylor vortices 110 formed in the annular channels when the rotor is actuated cause the fluid and components in the fluid to rotate as shown in FIG. 1 and increase the exposure of the fluid and components of the fluid to energy source 425.

The effects of flow rate, energy source location and cylinder rotation rate were considered for the inactivation of bacteria, for example *Escherichia coli*. These results are compared with similar data in a conventional channel. Details of the correlation of the data are also provided based on assumed inactivation kinetics and a plug flow reactor material balance. The latter analysis also introduces a new correction factor that accounts for the important boundary layer effects.

Another embodiment provides a Taylor-Couette reactor that provides excellent liquid surface renewal for the application of electromagnetic waves to chemical processing. The photoefficiency of such processes is affected by the penetration depth of radiation into the fluid relative to the velocity boundary layer thickness. The secondary flow caused by the presence of laminar vortices decreases the boundary layer thickness so that the dosage of radiation is substantially increased for fluids with large radiation absorptivities. In another embodiment, the maximum photoefficiencies occur when the radiation penetration depth is equal to the boundary layer thickness.

MATERIALS AND METHODS

Bacterial Culture

The *Escherichia coli* was obtained from the American Type Culture Collection, culture number 15597 (Manassas, Va.), The *E. coli* culture was grown and maintained on tryptic soy agar (TSA; Difco Laboratories) and tryptic soy broth (TSB; Difco Laboratories). *E. coli* was aseptically rehydrated using plates containing ATTC medium 271 agar at 37° C. for 24 hours. Colonies were transferred to agar slants and refrigerated at 4° C. For each experiment, colonies were aseptically transferred to a test-tube containing 10 mL Acumedia 7164A Tryptic Soy Broth. Test-tubes were placed in a Fisher Versa-Bath-S Model 224 temperature waterbath for 24 hr (37° C. and 30 rpm agitation rate). One mL of broth solution was diluted to 1-liter deionized water to obtain the $10^6$ CFU/mL influent.

Wastewater

To mimic the bacterial load in wastewater, simulated wastewater was spiked with $10^6$ CFU/mL of the indicator organism *Escherichia coli*. The wastewater was sampled and *E. coli* colonies were enumerated on tryptic soy agar in order to determine *E. coli* survival. To simulate wastewater, bentonite which is a colloidal silica of specific gravity of about 2.0 was added to establish a total suspended solids (TSS) concentration and turbidity, with full transmittance (FT) values no less than 55%, turbidity less than 2 to 3 NTU, and TSS less than 5 mg/L.

Taylor-Couette Flow

A Taylor vortex column was constructed of 4.6 cm internal diameter, fused quartz stator (Vycor) with a teflon rotor of 3.8 cm diameter by 13 cm in length as shown in FIG. 2. The resulting annular gap width d was 0.4 cm. The inlet consisted of one 6 mm tube located 13 mm from the bottom of the reactor. The irradiated holdup volume within the annular gap was 16.2 ml. Flow rates were varied from 13.1 to 136.8 ml/min. with a positive displacement pump. Four cold cathode, low pressure mercury UVC lamps with effective lengths of 3.1 cm [Gilway Technical Lamp. 2001. catalog #169.] were positioned equidistant around the outer quartz stator. In a second configuration the lamps were grouped 180 degrees from the inlet such that adjacent lamps were separated by a distance of approximately 2 mm as shown in FIG. 3B.

Lamps were surrounded with an aluminum reflector 225 as shown in FIG. 2. Lamp output (mW) was determined with an International Light IL1471A germicidal radiometer system (IL1400A monitor and SEL240/QNDS2/TD sensor) providing a spectral range of 185–310 nm and a measurement range of 33 $\mu$W/cm$^2$ to 330 mW/cm$^2$. Lamp intensity (mW/cm$^2$) was measured after lamps were energized for 20-minutes. When all four lamps were placed on the sensor with an aluminum reflector background, the intensity for the sensor area was recorded as 4.85 mW/cm$^2$. The intensity for all four lamps was further recorded as 4.0 mW/cm$^2$ at 1 cm from the sensor surface. The intensity of radiation for each lamp (wavelength~254 nm) was therefore rated at about 1 mW/cm at one cm from the lamp center.

The angular rotation of the rotor was controlled by a permanent magnet DC motor providing Taylor numbers over a range from 0<Ta<1000 where Ta=[Ud(d/R)$^{1/2}$]/$\nu$. Here, U=$\omega$R is the rotor surface velocity, the angular frequency to $\omega$=2$\pi$f, f is the rotor frequency, R is the rotor radius, d is the gap width and $\nu$ is the kinematic viscosity of the fluid.

Channel

A continuous flow reactor channel 500, 18.5 cm in length, including two PVC flow straighteners at both ends was constructed from a bronze 2×2 cm ID square. Centered in the channel 520 was a fused quartz capillary tube 510 as shown in the cross section of FIG. 5. The quartz tube 510 holds one cold cathode, low pressure, mercury UVC lamp 515 with a total effective irradiated length of approximately 7.8 cm. The intensity of radiation for the lamp (wavelength of about 254 nm) was about 1 mW/cm$^2$ at 1 cm from the center.

The irradiated volume of the reactor was 28.6 ml and the flow rates covered a range of values from 10<q<40 ml/min. The reactor Reynolds number covered the range 6<Re<25 for the indicated flow rates providing fully developed laminar flow in the cross sectional area. The cross sectional area of the channel is A$_c$=3.9 cm$^2$ with a hydraulic diameter of d$_h$=1.52 cm. An estimate of the laminar film thickness is $\delta$=d$_h$/4=0.38 cm that corresponds to the distance to the centerline of the asymmetric cross section.

Plug Flow Reactor

The following analysis is an adaptation of that presented by Severin et al. (Severin, B. F. et al. (1984) *Kinetic modeling of UV disinfection of water. Inactivation kinetics in a flow-through UV reactor*, J WPCF. 56:164–169) who considered a completely mixed flow-through reactor. Here, we consider a plug flow geometry also of annular design with a radiation source I$_o$ at radius r$_o$ along the axis. The kinetics of inactivation are assumed to be first order with respect to both the surviving organism density and the light intensity. Thus, the local disinfection rate R becomes $$R = KI(r)N(r,x) \qquad (1)$$

where

R=disinfection rate (organisms/cm$^3$-sec)
K=rate constant (mW-sec/cni$^2$)$^{-1}$
I(r)=radiation intensity at radius r, and
N(r,x)—surviving organism density at radius r and axial position x (organisms/cm$^3$).

From Lambert's law for a radiation source of infinite length, one obtains $$I(r)=(r_oI_or)\exp(-E(r-r_o)) \quad (2)$$

where $I_o$ is the radiation intensity at the quartz tube surface of radius $r_o$, E=2.3A and A is the solution absorbance.

A local material balance for the surviving organism concentration in an ideal plug flow reactor can be approximated in the form $$q(dN)=-KN(x)I(r)dV \quad (3)$$

where we have assumed that N is a constant with radius. Here, q is the volume flow rate and V=$\pi(r_f^2-r_o^2)$L is the volume of the reactor and dV=$2\pi$rdrdx. Substitution of Eq. (2) into Eq. (3) and integrating over $r_o<r<r_f$, one obtains $$dN/N=-mKI_o\tau dx/L \quad (4)$$

where N=N$_o$ at x=0 and $\tau$=V/q is the retention time. Thus, the outlet concentration of surviving organisms becomes $$N_f/N_o=\exp(-mKI_o\tau). \quad (5)$$

The dimensionless factor m in Eq. (5) is the ratio of the average light intensity in the reactor to the intensity at the surface of the quartz tube as derived by Severin et al. (Severin, B. F. et al. (1984) *Kinetic modeling of UV disinfection of water. Inactivation kinetics in a flow- through UV reactor*, J WPCF. 56:164–169) where $$m=2r_o[1-\exp(-E(r_f-r_o))]/[E(r_f^2-r_o^2)]. \quad (6)$$

It should be noted that for transparent fluids or E<1.0, m≅$2r_o/(r_o+r_o)$.

If the concentration of surviving organisms N is not constant with radius and a concentration boundary layer exists, then the argument of the exponent of Eq. (5) would be reduced by a factor n<1.0. This is the result of a reduced N in the local disinfection rate of Eq. (1) near the irradiated wall where the radiation intensity is the largest. Thus, one obtains $$N_f/N_o=\exp(-nmKI_o\tau) \quad (7)$$

where n is an empirical constant that is independent of axial distance for fully developed flow. Similar arguments were made in the study of photolytic reactions for such laminar plug flow geometries by Forney and Pierson (Forney, L J. and Pierson, J A. (2003b), Photolylic reactors: similitude in Taylor-Couette and channel flows, AIChE J. 49:1285–1292) which is incorporated herein in its entirety.

EXAMPLE 1

Taylor Number

Values for the inactivation of *E. coli* in the Taylor column were recorded at increasing rotation rates up to roughly 300 rpm corresponding to a Taylor number of 1000. The data shown in FIG. 6 indicate a minimum of a 4-log reduction in surviving *E. coli* in units of colony forming units per ml or cfu/ml at a value of Ta=100 or roughly 30 rpm (~0.5 Hz).

Figure 6:
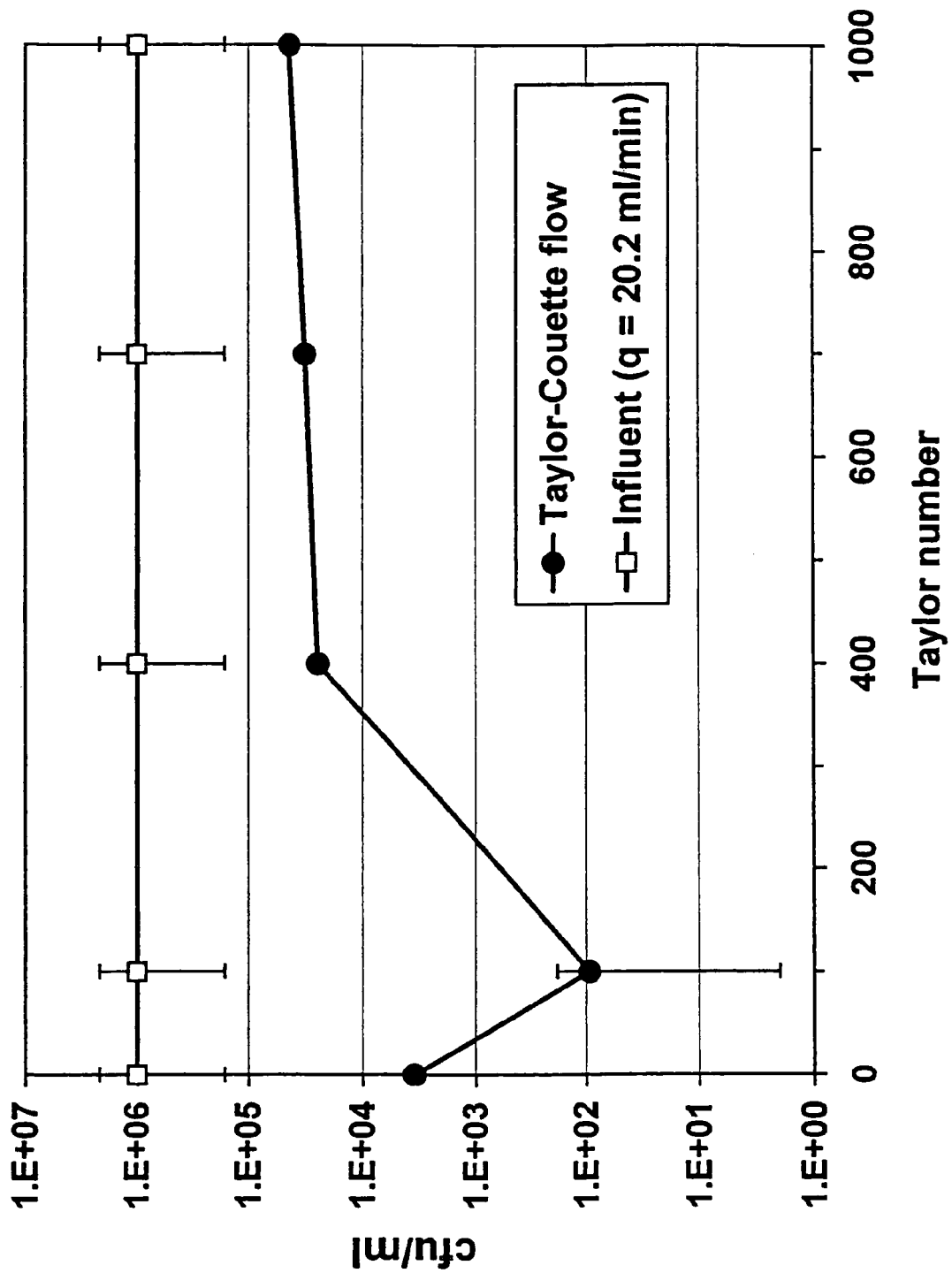
FIG. 6 is a line graph showing *E. coli* inactivation versus Taylor number.
Figure 7:
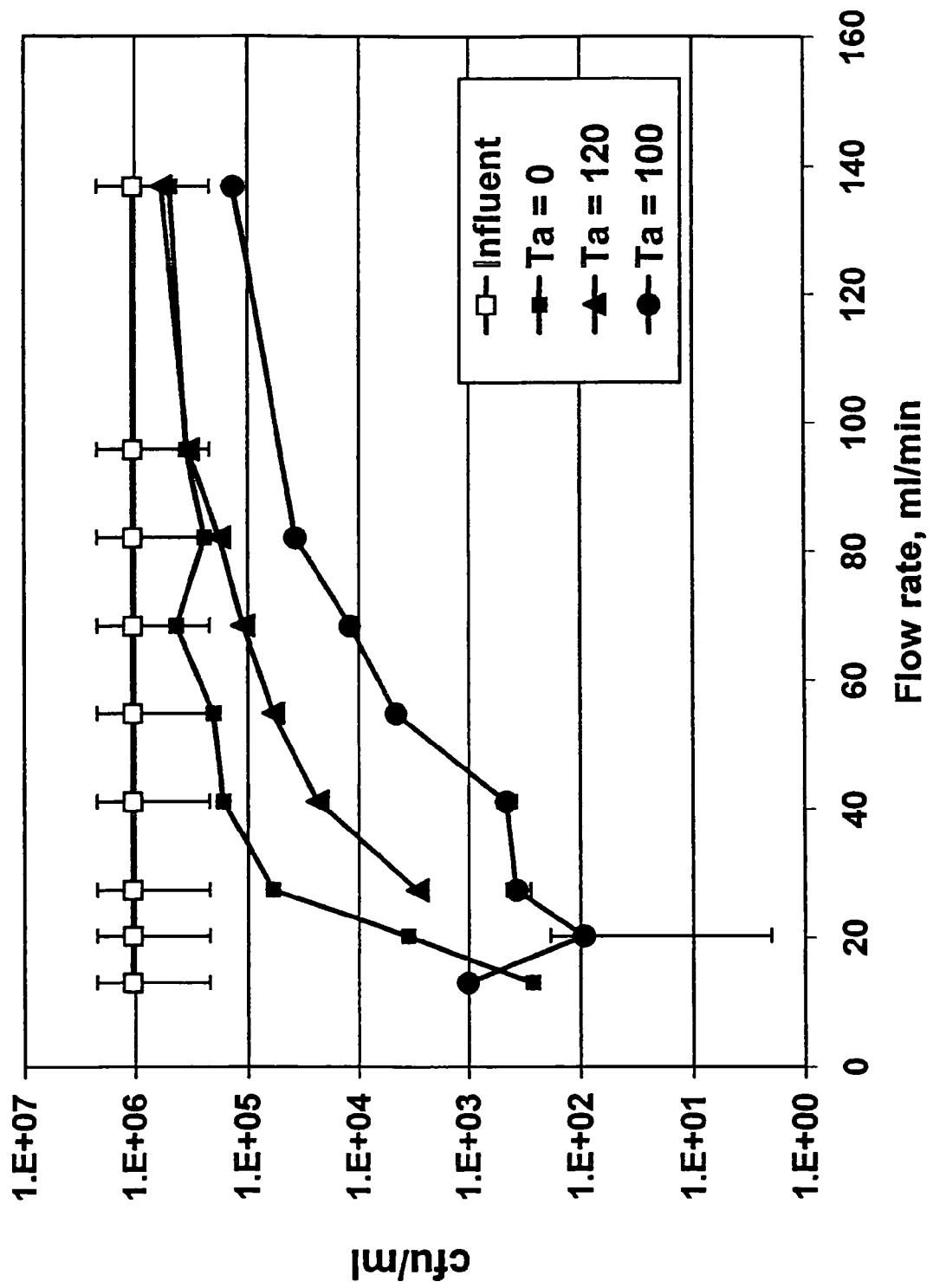
FIG. 7 is a line graph showing *E. coli* inactivation versus flow rate for various Taylor numbers. Ta=0 corresponds to flow between concentric cylinders.

Although the value of Ta=100 is somewhat above the critical value of Ta=41 for the onset of laminar Taylor vortices, Ta=100 represented an incremental reduction of roughly 1 or 2-logs in cfu/ml compared to other values of Ta with comparable flow rates as shown in both FIGS. 6 and 7. At Ta=400 the vortices become turbulent and the residence time distribution of the fluid broadens such that the characteristics of the Taylor column approach that of a completely mixed flow-through reactor. For values of 41<Ta<400 in the laminar range the reactor characteristics approach that of ideal plug flow with decreasing Ta.

As indicated in FIG. 6 the optimum rotation rate is in the laminar range of Ta. At higher rotation rates the bentonite is probably forced to the outer stator surface which in turn absorbs the applied UV radiation. All data recorded in the experiment constitute the average of at least two measurements of surviving *E. coli* for fixed operating conditions. The error bar for the data point at the minimum in FIG. 6 indicates the values for two independent measurements of *E. coli*. The remaining data with the same error or uncertainty of roughly 10$^2$ cfu/ml per point was insignificant compared to the larger concentrations of *E. coli* on the log plot. Also recorded in FIG. 6 are the influent concentrations of *E. coli* along with the expected error. The latter error was determined by measuring the *E. coli* concentrations both before and at the conclusion of the experiments.

EXAMPLE 2

Flow Rate

Values of *E. coli* inactivation were recorded at increasing flow rates for three values of the Taylor number Ta=0, 100 and 120. As indicated in FIG. 7 the inactivation levels decreased with higher flow rates for all values of Ta since the radiation dose $\propto 1/q$ where q is the volumetric flow rate through the reactor. A value of Ta=100 provides the largest inactivation rates for all recorded flow rates. Significantly, the plot also indicates an increase of over 2-logs for *E. coli* inactivation compared to simple flow through concentric cylinders (Ta=0) for moderate flow rates of 20 to 40 ml/min.

EXAMPLE 3

Lamp Symmetry

Figure 8:
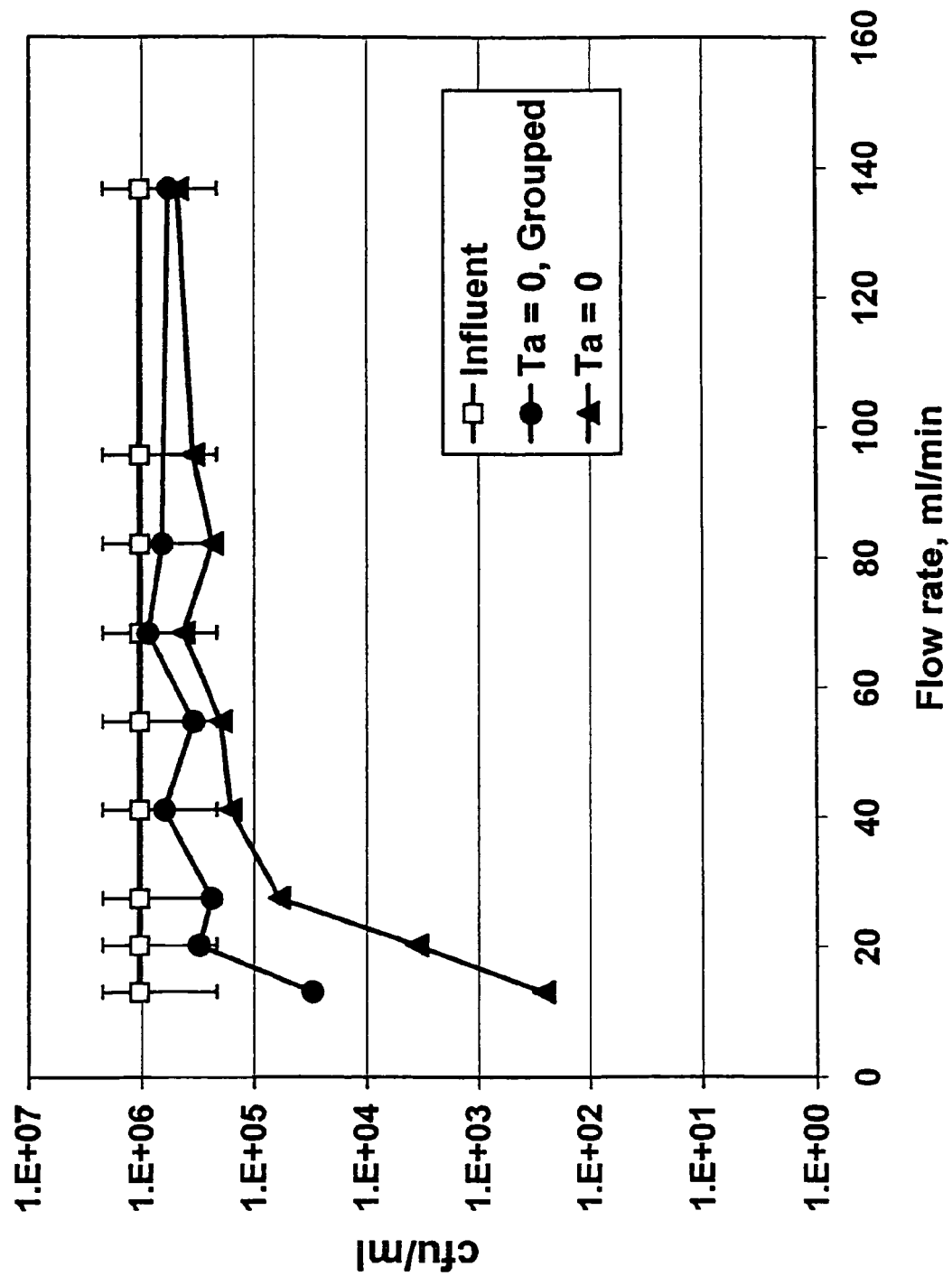
FIG. 8 is a line graph showing *E. coli* inactivation versus flow rate for symmetric and grouped lamp configurations. Ta=0 corresponds to flow between concentric cylinders.
Figure 9:
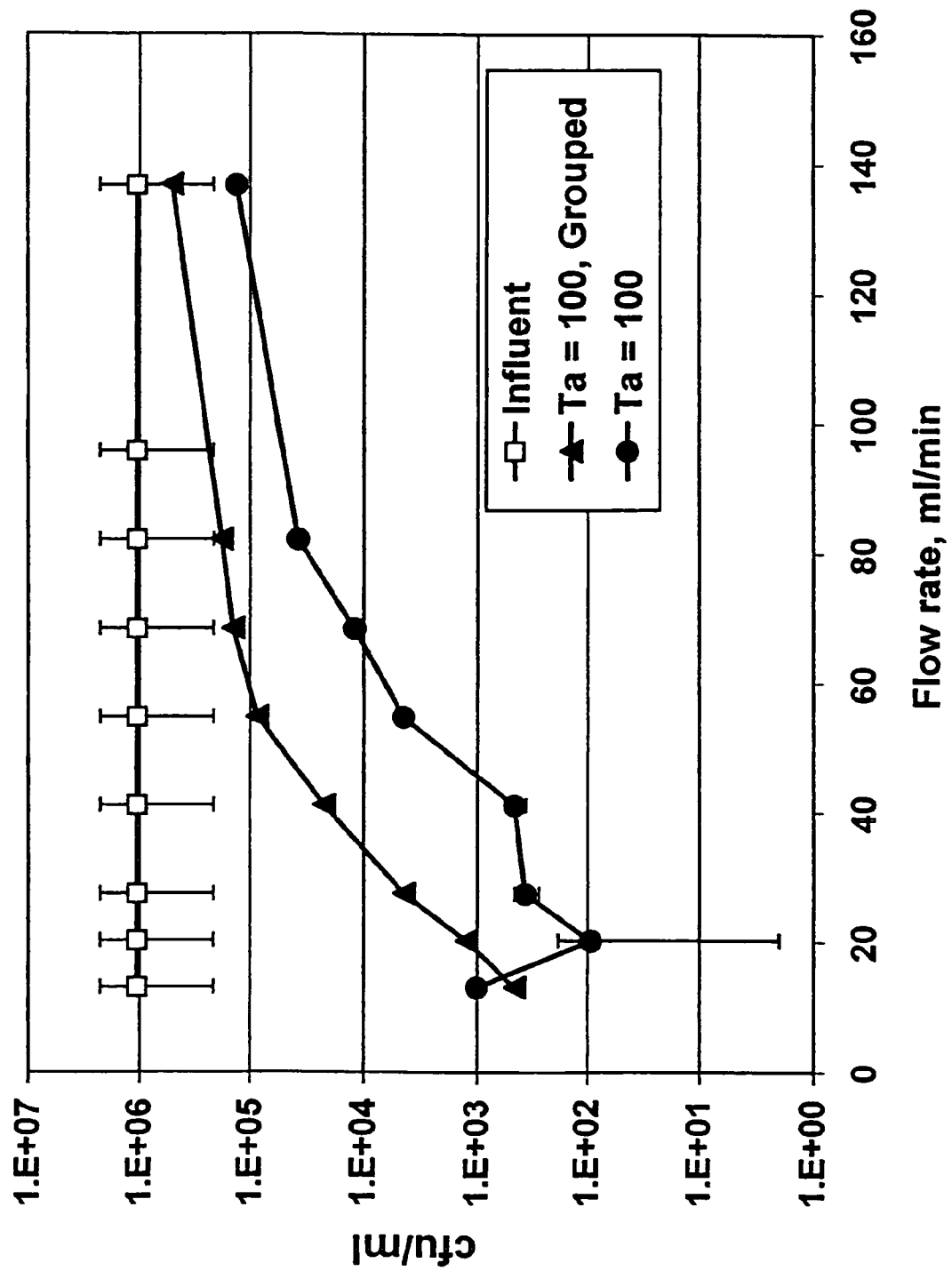
FIG. 9 is a line graph showing *E. coli* inactivation versus flow rate for symmetric and grouped lamp configurations. Ta=100 corresponds to Taylor-Couette flow.

The effects of lamp location on inactivation were measured and the data are recorded in FIGS. 8 and 9. FIG. 8 with no rotation or Ta=0 demonstrates that channeling of the pathogens occurs between concentric cylinders when the lamps are grouped on the side of the reactor opposite the fluid inlet.

For the symmetrical case of equidistant lamp location and at Ta=100, FIG. 9 illustrates that an improvement of over a 1-log reduction in surviving organisms was again observed compared to the grouped geometry for moderate flow rates between 20<q<60 ml/min. Moreover, the improvement was somewhat less than 1-log at higher flowrates q>60 ml/min at lower photon dosages. One concludes that there is a significant loss of photons from both reflection and transmission through multiple lamps in close proximity,

EXAMPLE 4

Dosage

Figure 10:
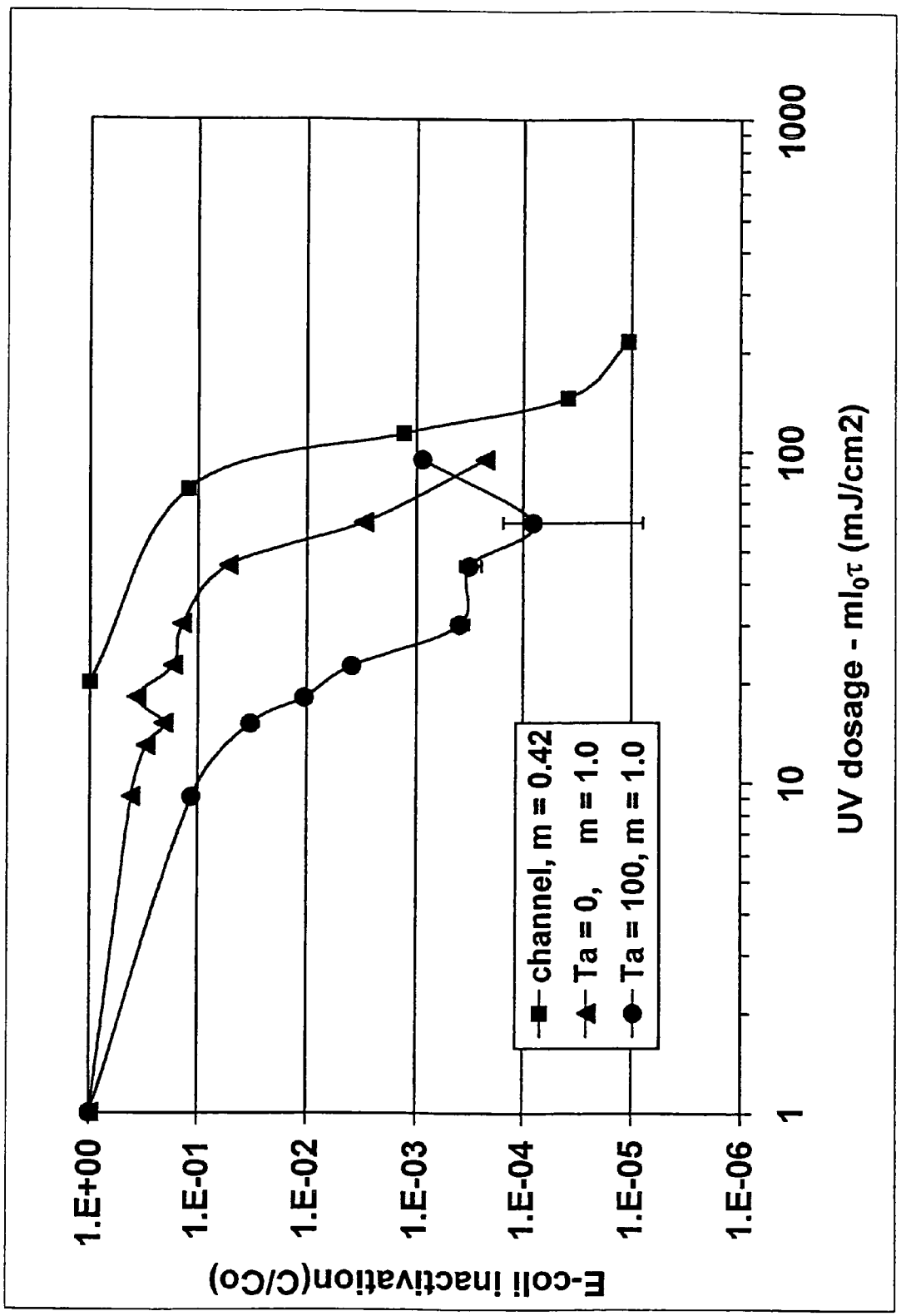
FIG. 10 is a line graph showing fractional *E. coli* inactivation versus UV dosage.

The inactivation of E. coli was measured for the channel and the data are compared in FIG. 10 to the results taken with the Taylor column at Ta=0 and 100. In FIG. 10 the UV dosage was computed based on the average radiation intensity within the fluid times the fluid residence time. The value of m defined by Eq. (6) that represents the ratio of average intensity within the fluid-to-the quartz surface value was estimated from the approximation $m=2r_o/(r_o+r_f)=0.42$ for low fluid absorbance where $r_f$ is equal to the radius of a circle with the same cross sectional area as the square channel in FIG. 5. The corresponding values of m for the annular gap in the Taylor column were estimated to be m=1.0 since the lamps were located outside the gap with photo reflection inward toward the rotor.

Figure 5:
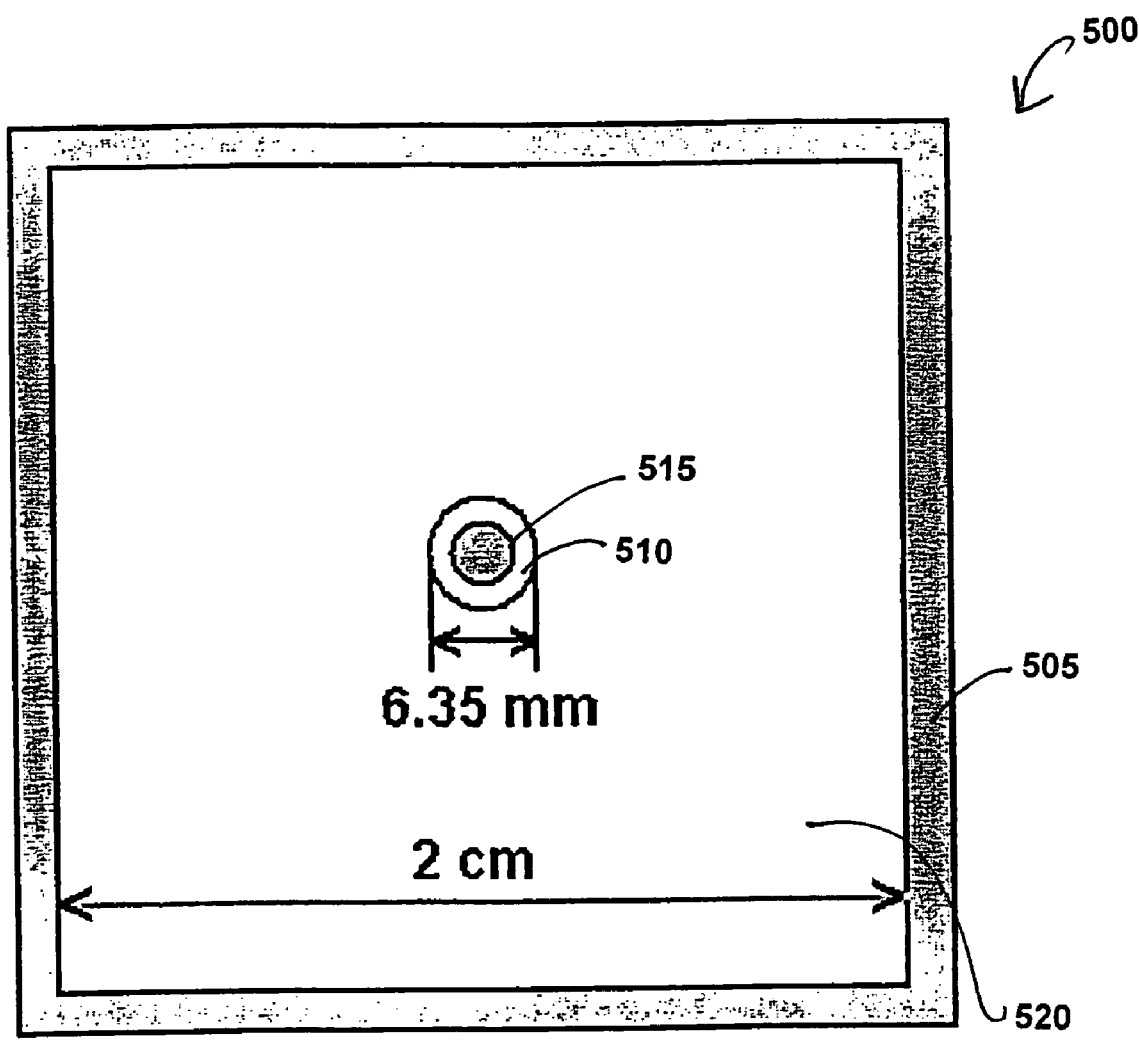
FIG. 5 is a diagram of a square reaction channel.

The lamp intensity $I_o$ in units of mW/cm² at the quartz tube surface for the channel in FIG. 5 was computed from the lamp length and tube diameter. To compute $I_o$, the total mW output from the 7.8 cm effective lamp length was divided by the quartz tube surface area. Similarly, to compute the average light intensity $I_0$ of the inside surface of the quartz stator in the Taylor column, the total lamp output in mW for 4 lamps with an effective length of 3.1 cm per lamp was divided by the total surface area computed from the inside diameter of the quartz stator (length of 3.1 cm). The intensity of radiation for both the channel and the Taylor column were based on an assumed absorption of 6% for the quartz tube (GE 124) and 27% for the quartz stator (Vycor Coming 7913), respectively.

The results in FIG. 10 indicate more than a 3-log reduction in the inactivation of E. coli with Taylor-Couette flow compared to a conventional channel at moderate flow rates of 20<q<40 ml/min. These conclusions are based on an equal radiation dosage in units of mJ/cm² within the fluid.

EXAMPLE 5

One of the major problems that one must contend with during the continuous use of UV reactors is the maintenance requirement of both cleaning the numerous lamp surfaces from fouling and replacement of defective lamps. The use of Taylor-Couette flow provides repetitive contact of fluid parcels with a minimum number of lamps. For example, in one embodiment described herein operating at Ta=100, with four lamps and a flow rate of 20 ml/min, a given fluid parcel will make roughly 25 revolutions before reaching the outlet. Therefore, with four lamps per revolution, a parcel of fluid therefore makes contact with the equivalent of 100 lamps as it passes through the Taylor column.

Figure 11:
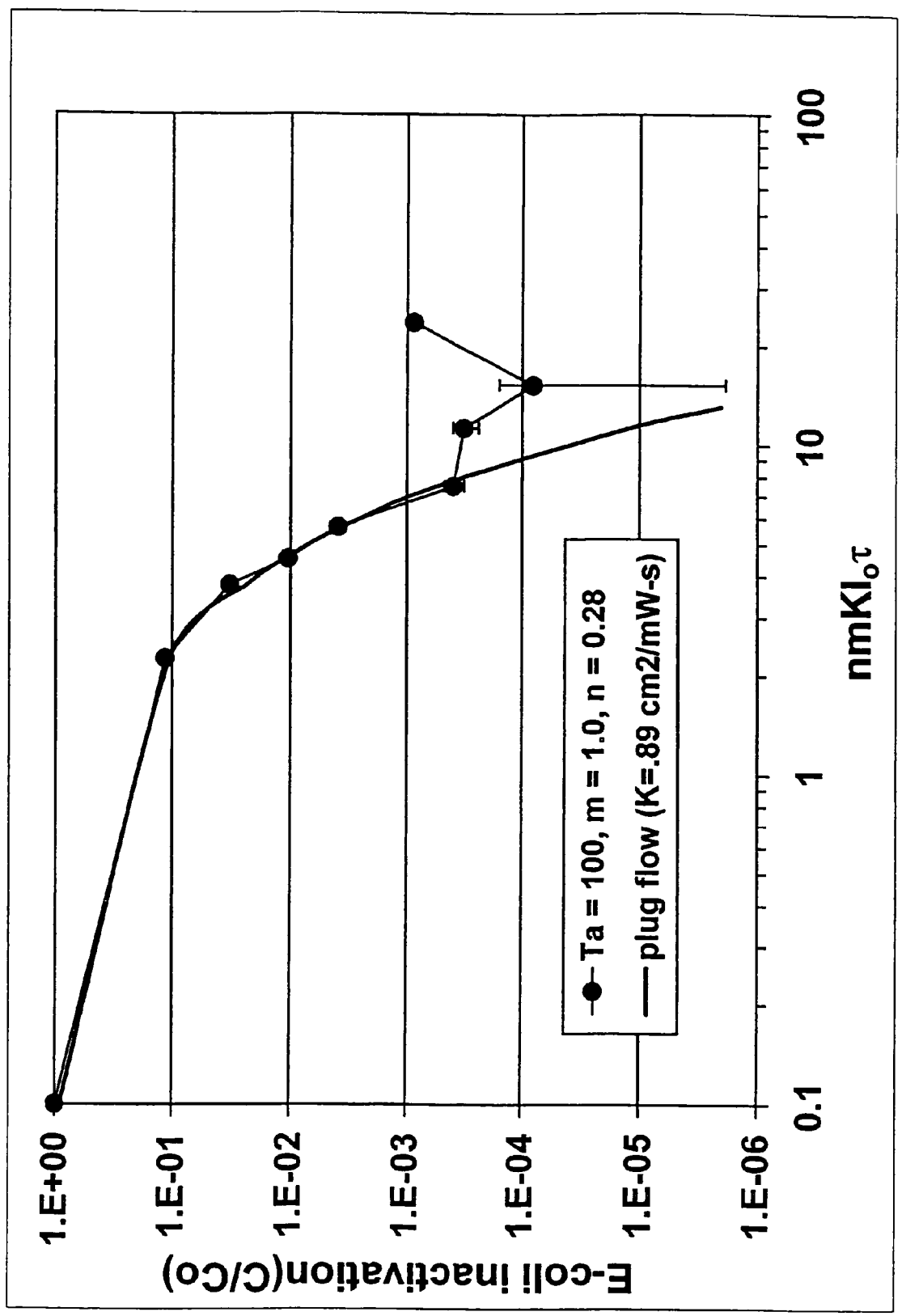
FIG. 11 is a line graph showing fractional *E. coli* inactivation versus dimensionless UV dosage for Taylor-Couette flow; n is the correction factor for the effects of the concentration boundary layer; m is the ratio of the average fluid UV intensity-to-the intensity at the quartz lamp surface; $I_o$ is the average UV intensity at the lamp surface; K is the inactivation rate constant for *E. coli*.

The optimum inactivation data for Ta=100 with the Taylor column can be replotted in the form suggested by Eq. (7). The inactivation rate constant for E. coli or K=0.89 cm²/mW-s that appears in the independent variable $nmKI_o\tau$ was substituted from the batch inactivation data from (Severin, B. F. et al. (1984) *Kinetic modeling of UV disinfection of water. Inactivation kinetics in a flow-through UV reactor*, J WPCF. 56:164–169). The remaining value of the boundary layer, correction factor n can be estimated by comparison with the data. The resulting plot is shown in FIG. 11 which is data replotted from FIG. 10 with a value of n=0.28 in Eq. 1 that places the theory through the first six data points. As illustrated in FIG. 11, all of the fractional inactivation data appear to conform to the model of a plug flow reactor with the exception of those data taken at the low flowrates near q=20 ml/min on the left of FIG. 10. These latter data are subject to both the effects of the centrifugal forces leading to an increase in the bentonite concentrations near the transparent stator surface and to gravitational settling of the silica colloid at the inlet passage.

Figure 12:
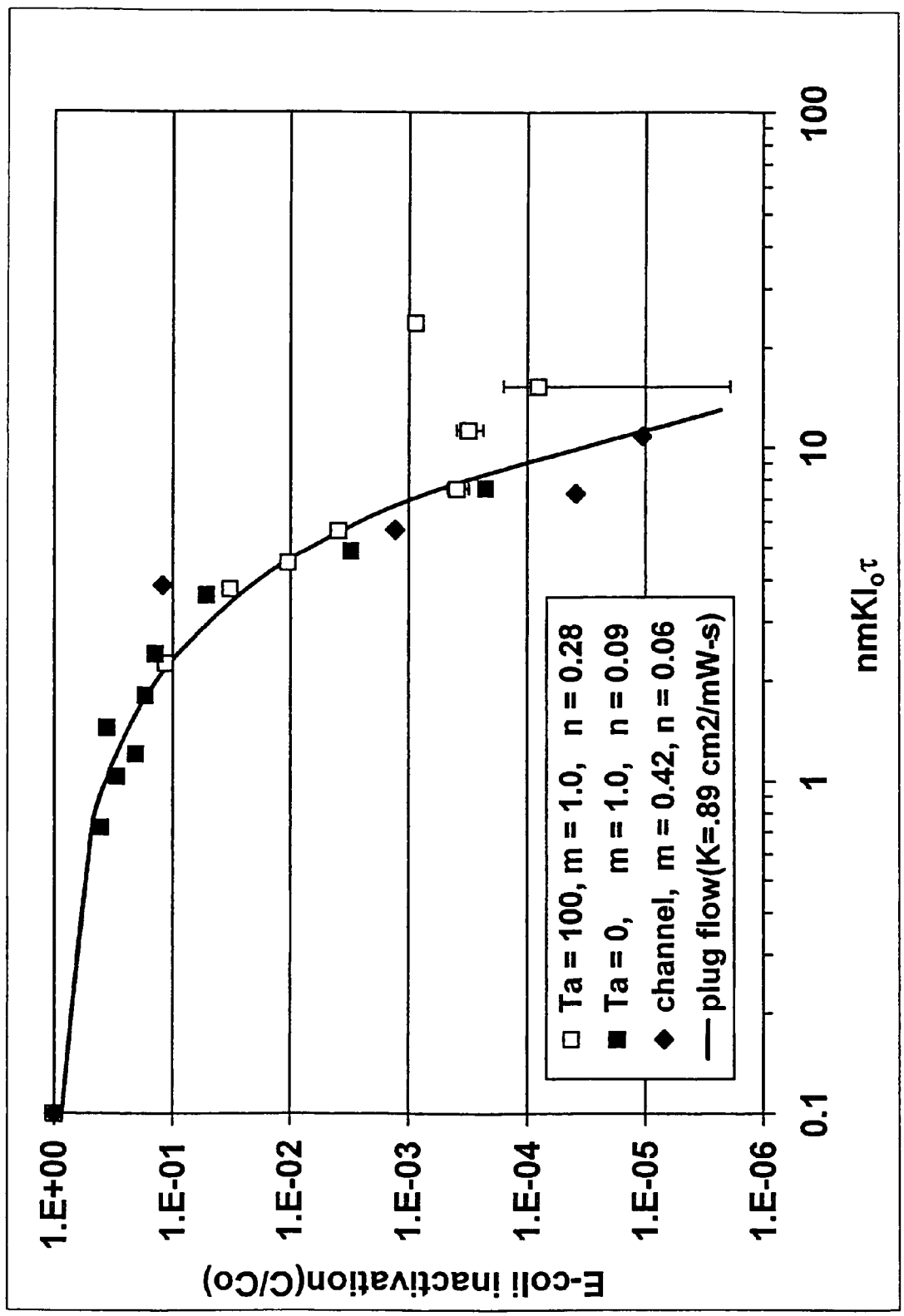
FIG. 12 is a line graph showing fractional *E. coli* inactivation versus dimensionless UV dosage for Taylor-Couette flow (Ta=100). The flow between concentric cylinders (Ta=0) and channel flow. Parameters are the same as in FIG. 11.

In a similar fashion, all of the data of FIG. 10 were replotted in FIG. 12 with estimates of the boundary layer, correction factor n for each case as shown in the figure caption. Again, all of the data appear to conform to the plug flow model. It is interesting to note that estimated values of n in FIG. 11 appear to decrease with increasing boundary layer thickness. The latter observation conforms to the earlier work of Forney, L. J. and Pierson, J. A. (2003), *Photolylic reactors: similitude in Taylor-Couette and channel flows*, AIChE J. 49:1285–1292 which suggests that the yield from photolytic reactions in fully developed laminar reactors $n \propto 1/\delta$ where $\delta$ is the velocity boundary layer thickness or that $n \propto 1/\delta$ in Eq. (7).

Table 1 shows a comparison with the empirical values of n used in FIG. 12 with the expression $n=0.023/\delta$. The empirical values of n were chosen in FIG. 12 and Table 1 such that there were an equal number of data points both above and below the theory. Moreover, in Table 1 the values of the velocity boundary layer thickness 5 were taken from Forney, L. J. and Pierson, J. A. (2003), *Photolylic reactors: similitude in Taylor-Couette and channel flows*, AIChE J. 49:1285–1292 where 8 was estimated to be dh/4 for both the channel and the case of flow between a concentric cylinders (Ta=0) where dh is the hydraulic diameter. The value of 5 for the case Ta=100 was estimated to be on the order of $Ta^{-1/2}$ (Forney, L. J., and Pierson, J. A. (2003) *Optimum photolysis in Taylor-Couette flow*, AIChE J. 49:727–733).

The common problems of non-uniform radiation levels and concentration boundary layer effects are largely eliminated in UV reactors with the use of Taylor-Couette flow that is the hydrodynamic equivalent to cross flow over a tube bank (Baier, G. et al. (1999). *Prediction of mass transfer in spatially periodic systems*, Chem. Eng. Sci. 54:343) or for this application a lamp array. Moreover, the repetitive exposure of fluid parcels to a small number of lamps decreases maintenance requirements. Over a 3-log reduction in the inactivation of E. coli under the best conditions was demonstrated compared to a conventional channel with the same radiation dosage. Moreover, greater than a 2-log reduction was evident compared to flow through concentric cylinders.

The inactivation data for three reactor geometries of Taylor-Couette flow and flow between either concentric cylinders or a square channel are correlated with the assumption of plug flow. In particular, the effects of non-uniform radiation levels are accounted for by integration across the fluid channel as done in the past but a new correction factor is introduced that is inversely proportional to the velocity boundary layer thickness to account for the effects of a concentration boundary layer.

TABLE 1

Prediction of Boundary Layer Correction Factor-n

| | | n | |
|---|---|---|---|
| Flow Geometry | Boundary Layer Thickness - δ(cm) | 0.023/δ | empirical (FIG. 11) |
| Taylor-Couette Ta = 100 | 0.08 | 0.28 | 0.28 |
| Concentric Cylinders | 0.2 | 0.11 | 0.09 |

TABLE 1-continued

Prediction of Boundary Layer Correction Factor-n

| Flow Geometry | Boundary Layer Thickness - δ(cm) | 0.023/δ | empirical (FIG. 11) | n |
|---|---|---|---|---|
| Ta = 0 | | | | |
| Channel | 0.38 | 0.06 | 0.06 | |

EXAMPLE 6

Photochemistry

Fast UV photolysis of aqueous iodide producing triiodide was also investigated. Concentrated KI solutions are optically opaque at wavelengths of 254 nm and act as photon counters. UV absorption by iodide leads to an aqueous or solvated electron via a charge transfer-to-solvent reaction and the formation of an excited iodine atom The essential reactions are listed below, $$I^- + h\nu \rightarrow I + e^- \tag{8}$$

$$I + e^- \rightarrow I^- \tag{9}$$

$$2I^* + I^- \rightarrow I_3^- \tag{10}$$

As noted, the UV-induced formation of triiodide is potentially limited by the back reaction of Eq. (9). The quantum yield for triiodide is significantly increased, however, by the addition of potassium iodate. In the presence of iodate, scavenging of the bulk electron occurs and the following additional reaction is proposed $$IO_3^- + e^- + 2H_2O \rightarrow IO^- + H_2O_2 + OH^* + OH^- \tag{11}$$

The yield of the triiodide photoproduct is easily monitored by spectrophotometry at either 350 or 450 nm depending on the concentration. The quantum yield of φ=0.75 mol./einstein is relatively constant with either temperature or reagent iodide concentrations. With the addition of a borate buffer (pH 9.25) to minimize thermal oxidation, stock solutions of 0.6 M KI and 0.1M $KIO_3$ with the borate buffer are stable and insensitive to ambient light in the visible spectrum. Radial mass transfer in Taylor-Couette flow has been documented in terms of a Sherwood number Sh of the form $$Sh \alpha Ta^{1/2} Sc^{1/3} \tag{12}$$

where the Taylor number $$Ta = (\omega R d/\nu)(d/R)^{1/2}. \tag{13}$$

The indicated exponents in Eq. (12) were determined previously by a number of experiments and also confirmed by the recent numerical predictions. The torque coefficient CM for Taylor-Couette flow is of the form $$C_M = 2M/(\pi \rho \omega^2 R^4 h) \alpha Ta^{-1/2} \tag{14}$$

for the range of Taylor numbers $Ta_c < Ta < 400$ where the critical Taylor number $Ta_c = 41$ indicates the onset of laminar vortices. Here, the moment $M = \tau(2\pi R^2)$ and τ is the shear stress on the rotor.

Equations (12) and (14) suggest that the transport coefficients in laminar, Taylor-Couette flows are correlated by a Chilton-Colbum analogy of the form $$J_D = Sh/(Ta Sc^{1/3}) = C_M/2 \tag{15}$$

For the values 40<Ta<400 and the Schmidt number Sc=ν/D>1, These conclusions are consistent with laminar and heat transfer correlations on a spinning disc but with Ta replaced by the Reynolds number based on the disc angular velocity and diameter.

Consider now a laminar boundary layer with a linear velocity and concentration profile (film model) on the surface of a Taylor-Couette flow (Ta>$Ta_c$) Since the mass transfer coefficient $k_c \alpha D/\delta_c$, and the Sherwood number $$Sh \alpha k_c d/D \tag{16}$$

where $\delta_c$ is the concentration boundary layer thickness, d is the gap width and D is the solute molecular diffusivity, one obtains $$Sh \alpha d/\delta_c \alpha (d/\delta)(\delta/\delta_c). \tag{17}$$

Since a boundary layer analysis confirmed by experiment suggests $\delta_c/\delta \alpha Sh^{1/3}$, one obtains a ratio of characteristic reactor length d-to-velocity boundary thickness $$d/\delta \alpha Ta^{1/2} \tag{18}$$

for Ta>$Ta_c$.

Attempts to obtain Eq. (18) by stretching the characteristic lengths d or δ for a boundary layer on a flat plate by a factor of $(d/R)^{1/2}$ were unsuccessful. There is some evidence, however, that the Sherwood number $Sh \alpha Ta^{1/2} Sc^{1/3}(d/R)^{0.17}$ from the mass transfer experiments of Holeschovsky and Cooney but, again, the exponent magnitude of 0.17 is inconsistent with the attempted boundary analysis that would suggest larger values.

Fast photochemical reactions must occur near transparent reactor walls. The thickness of the reaction layer, however, is not confined to a fraction of the velocity boundary thickness, but rather to the radiation penetration depth. The latter depth, in fact, can exceed both the boundary thickness or characteristic reaction dimension depending on the absorbance of the reacting solution.

Since the solution absorbance is defined by $$A = A \epsilon C \tag{19}$$

where the intensity of radiation is $I/I_o = 10^{-A}$, ε is the extinction coefficient, C is the absorbing species and A, is the radiation depth, the reaction layer is therefore confined to a layer on the order of $$A \alpha I/\epsilon C. \tag{20}$$

An additional dimensional parameter is the maximum possible concentration of photochemical product formed. The latter is equal to the product of the number of photons introduced into the reactor and the quantum efficiency of the reaction. The maximum concentration of product formed is thus $$Cm = n I_o A_1 \phi / \gamma q \tag{21}$$

where n is the number of lamps, $I_o$, is the intensity of radiation [W/cm2], $A_1$ is the area of a single lamp, φ is the reaction quantum efficiency [mol product/einstein], q is the reactor volume flow rate and γ[J/einstein] is the conversion factor from a mol of photons to joules of energy.

Dimensional arguments suggest that the concentration of photochemical product formed $C_\omega$ is of the form $$C_\omega/C_i(I) \alpha f(Cm/C_i(I), \lambda/\delta) \quad (22)$$

provided the Taylor number Ta>0 where $C_i(I)$ is the concentration of reactant iodide in the inlet stream. Simplifying Eq. (22) somewhat since a mass balance implies $C_\omega \alpha Cm$, one obtains $$C\omega/C_i(I) \alpha Cm/C_i(I)[f(\lambda/\delta)]. \quad (23)$$

Defining Co as the product concentration with no rotation, one now obtains an expression which isolates the effects of rotation in the form of the dimensionless quantity $$(C\omega - Co)/Co = f(\lambda/\delta) \quad (24)$$

Another embodiment provides a Taylor vortex column having a bronze rotor 3.43 cm in diameter by 5 cm in length centered within a fused quartz beaker with an inside diameter of 4.1 cm providing a gap width of d=0.334 cm. The holdup volume (irradiated) was 12 ml with a range of flow rates between 15<q<50 ml/min. Five cold cathode, low pressure mercury UVC lamps with effective lengths of 3.1 cm were positioned around the quartz beaker and surrounded by an aluminum reflector with an over 90% reflectivity of UV radiation. The intensity of radiation for each lamp (wavelength ~254 nm) was rated at 1.7 mW/cm2 at the lamp surface providing a range of power input from 0.033 W to 0.164 W depending on the number of lamps engaged.

A solution of 0.6 M potassium iodide (KI) and 0.1 M potassium iodate ($KIO_3$) buffered (pH 9.25) with borate was pumped through the Taylor column. The absorbance of triiodide at the outlet was measured at either 350 or 450 nm for low or high concentrations, respectively, depending on the number of lamps engaged or liquid flow rate. The rpm of the rotor, controlled by a permanent magnet DC motor, was varied between 0<rpm<75 providing a Taylor number covering the range 0<Ta<200.

The triiodide absorbance as expected, clearly indicated a large increase of roughly 60% for Taylor numbers Ta>$Ta_c$ where the lower limit of $Ta_c$=40 corresponds to the onset of Taylor vortices at low axial Reynolds numbers. Since the cross sectional area for the flow within the gap is 4 $cm^2$, the axial Reynolds number was Re<10 for all experiments and thus had no effect on the critical $Ta_c$.

Plug Flow Reactor

When the Taylor number Ta>$Ta_c$ and laminar vortices are present within the Taylor column, the flow can best be described as approximating that of an ideal plug flow reactor. Assuming a zero order rate expression at steady—state. one obtains $$udC/dx = r \quad (25)$$

where the constant rate[mol/liter-s]

$$r = nI_\sigma A_l \phi / \gamma V \quad (26)$$

and V is the holdup volume of the reactor Thus, the concentration of triiodide formed from Eq. (25) with dx/u=dV/q is $$C(I_3) = \beta rV/q \quad (27)$$

where the factor $\beta << 1$ accounts for both the loss of input radiant energy to liquid heating and surface absorption and the effects of back reactions from triiodide to iodide depleting the product as described later.

Normalized plots of Eq. (23) for the outlet triiodide concentration for increasing flow rates at fixed rpm (Ta=100) and the standard stock solution (0.6 M iodide) where Cm is defined by Eq (14) show that the photo efficiency of the reactor is not high (<30%) so that axial variations in the iodide reactant and thus the radiation penetration depth are small consistent with the analysis.

Effects of Rotation

The effects of rotation are isolated by comparing the product concentration at fixed Taylor numbers Ta>$Ta_c$ with the product formed at zero rpm or Ta=0. Because of the large surface-to-volume ratio for the reactor, one would expect a considerable enhancement in the magnitude of the transport coefficients without vortices. A nearly constant 70% improvement in product yield occurs for all Ta>$Ta_c$ Percentage increase in reaction product at fixed Ta=100 for various values of the radiation dosage were obtained by engaging one to five UV lamps and changing the flow rate between 16 and 32 ml/min. There is some scatter in the data possibly due to channeling through the reactor for the Ta=0 case, since the reactor inlet and outlet were located on the same side but 45° apart. Thus, the sequence of lamps in the circumferential direction was varied for several experiments with the same total power input leading to the indicated scatter. However, it is apparent from the data that the concentration of product formed due to rotation is independent of the dosage of radiation supplied as suggested by Eq. (24).

Optimum Rotation

The similarity law proposed by Eq. (24) was tested by varying the reactant concentration, that is, the concentration of iodide fed to the reactor inlet. Since the absorbance A=$\lambda \epsilon C_i(I)$ is 200 for a 0.6 M KI and 0.1 M $KIO_3$ solution, the extinction coefficient e at a wavelength of 254 nm was calculated to be $\epsilon=333$ $M^{-1}cm^{-1}$. Setting the absorbance A=1 that represents a radiation depth over which 90% of the UV photons are absorbed, one calculates the radiation depth to be $\lambda=1/\epsilon C_i(I)$.

The stock solution of 0.6 M KI and 0.1 M KlOs along with a series of additional solutions with KI and $KlO_3$ in the same ratio but diluted by a factor of up to 100 were fed to the reactor. The product triiodide concentration was measured at both Ta=0 and 100 for each inlet solution. The data show that the reaction yield is inhibited if the reaction layer lies within the velocity boundary layer or $\lambda/\delta << 1$ (see FIG. 1B). Under these circumstances the large concentration of $I_3^-$ within the boundary is reduced by the solvated electron $e_{aq}^-$ back to $I^-$ via the reaction

$$e_{aq}^- + I_3^- \rightarrow I_2^- + I^- \quad (28)$$

and the product yield of K is diffusion limited.

Figure 13:
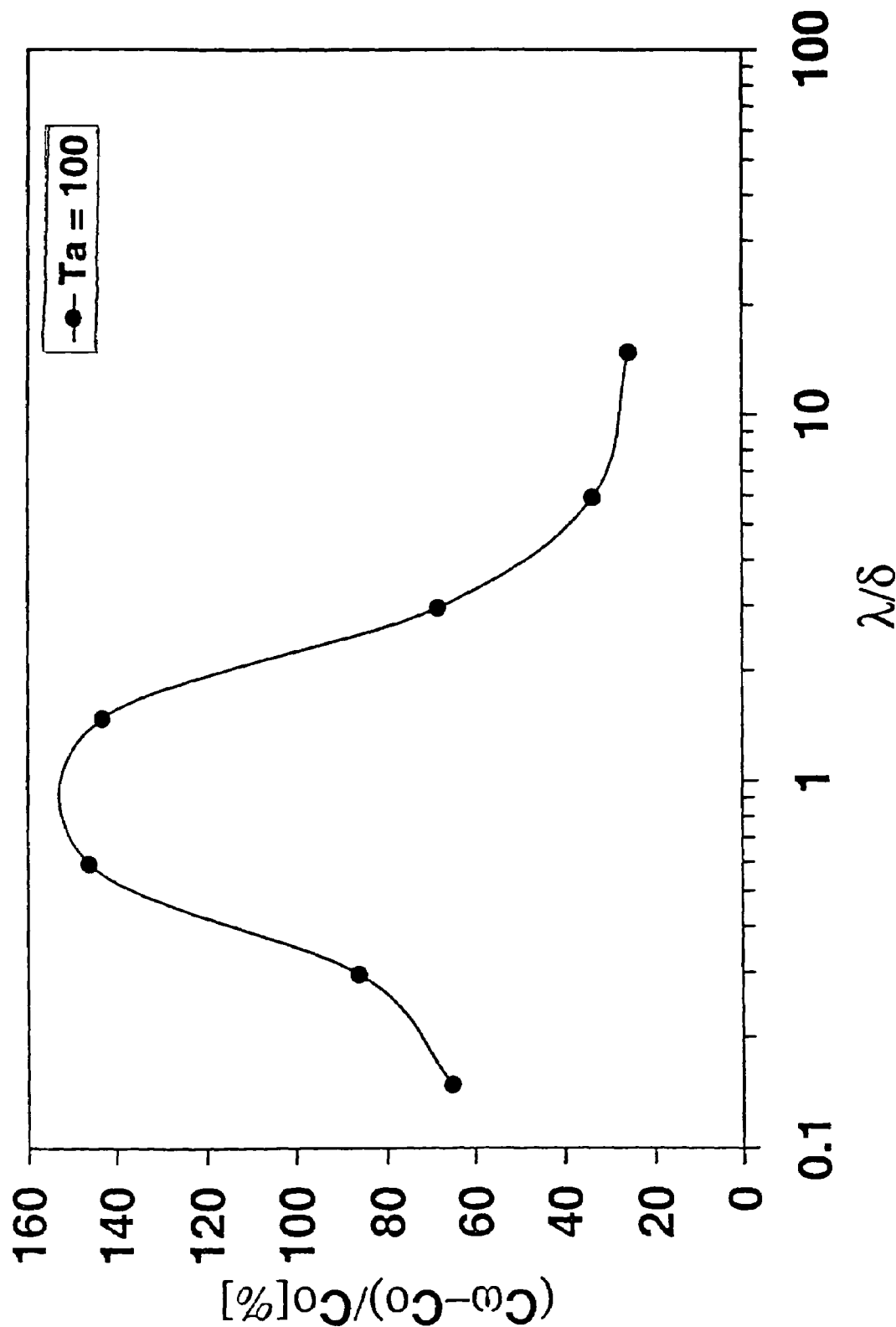
FIG. 13 is a line graph showing the percent change in outlet triiodide concentration versus the ratio of radiation penetration depth to velocity boundary layer thickness.

FIG. 13 shows the percent change in outlet triiodide concentration versus the ratio of radiation penetration depth to velocity boundary layer thickness. If the reaction layer thickness is greater than the velocity boundary layer or $\lambda/\delta >> 1$, the product $I_3^-$ is formed throughout the gap and the advantages of the circulating vortices are substantially reduced. It should be noted that the left data point in FIG. 13 corresponds to a reaction layer that is 15% of the velocity boundary thickness where the latter is 10% of the gap width d. In contrast, the right data point in FIG. 13 represents a radiation depth that is 150% of the gap width d. At the optimum operating conditions $\lambda/\delta=1$ one obtains a maxi mum 150% increase in the product concentration. Under the latter constraint if $$\lambda/\delta=Ta^{1/2}/(d\epsilon C_i(I)) \qquad (29)$$

selling $\lambda/\delta=1$, one obtains an optimum frequency $f_{op}$ Hz of rotation equal to $$f_{op}=(\nu/2\pi)(dR)^{1/2}\epsilon^2 C_i^2(I)$$

Scale-Up

An efficient UV reactor requires multiple exposure of the pathogen to a fixed number of lamps positioned around the reactor circumference. The number of cycles of the pathogen around the axis of the reactor as the pathogen passes from inlet to outlet is N where $$N=ft_r$$

and f is the rotor frequency (cycles/sec) and $t_r$ is the fluid residence time or $$t_r=V/q=\pi Ddh/q$$

Here, h is the rotor length, d is the gap width, D (=2R, see FIG. 1A) is the rotor diameter, q is the fluid flowrate and V is the volume of fluid within the annular gap. The number of cycles N can be rewritten in the form $$N=Ta(D/2d)^{1/2}\nu h/q$$

Thus, for fixed Taylor number Ta and gap width d such that the ratio of radiation penetration depth-to-boundary layer thickness $\lambda/\delta$ is a constant and for fixed fluid properties $\nu$, one obtains $$N\alpha D^{1/2}h/q$$

Thus, scale-up of the reactor to larger rotor diameters D and longer rotors h is achieved for fixed N if $$q\alpha D^{1/2}h$$

It should be emphasized that the above-described embodiments of the present invention, particularly, any "preferred" embodiments, are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention and protected by the following claims.

What is claimed is:

1. A fluid reactor comprising:
   an outer cylinder;
   a rotor having a first annular channel between an outer wall and an inner cylinder, wherein the rotor is housed within the outer cylinder,
   the outer cylinder having:
      an inner annular wall defining a circular hollow for receiving the inner cylinder of the rotor, and
      an outer annular wall defining a second annular channel between the outer annular wall and inner annular wall for receiving the outer wall of the rotor;
      an inlet in fluid communication with the second annular channel; and
      an outlet in fluid communication with the circular hollow.

2. The reactor of claim 1, wherein the outer cylinder further comprises an energy source.

3. The reactor of claim 2, wherein the energy source provides electromagnetic energy.

4. The reactor of claim 3, wherein the electromagnetic energy irradiates fluid in the reactor.

5. The reactor of claim 4, wherein the electromagnetic energy is provided in an anti-microbially effective amount.

6. The reactor of claim 2, wherein the energy source is a lamp for providing ultraviolet light.

7. The reactor of claim 1, wherein Taylor-Couette flow is established in fluid within the reactor when the rotor is rotated within the outer cylinder.

8. The reactor of claim 7, wherein the Taylor-Couette flow comprises a plurality of circumferential vortices within the first and second annular channels.

9. The reactor of claim 1, wherein the outer wall of the rotor is transparent.

10. The reactor of claim 1, wherein the inner and outer annular walls of the outer cylinder comprise an energy source.

11. A method of disinfecting a fluid comprising:
   forming Taylor vortices in an edible fluid comprising an organism, wherein the edible fluid has a Taylor number of between about 40 to about 400; and
   irradiating the fluid with an anti-microbial amount of energy, wherein the ratio of penetration depth of the enemy to a velocity boundary layer of the edible fluid is less than about 1.

12. The method of claim 11, wherein the anti-microbial amount of energy is about 400 J/m².

13. The method of claim 11, wherein the Taylor number is from about 75 to about 125.

14. The method of claim 11, wherein the organism comprises bacteria, fungi, protozoa, viruses, or a combination thereof.

15. The method of claim 11, wherein the energy is electromagnetic energy.

16. The method of claim 11, wherein the edible fluid comprises milk, fruit juice, or a beverage.

17. The method of claim 11, wherein the ratio of penetration depth of the energy to the velocity boundary layer is from about 0.5 to about 1.

* * * * *